(12) United States Patent
Dionne et al.

(10) Patent No.: US 10,071,383 B2
(45) Date of Patent: *Sep. 11, 2018

(54) HIGH-VOLUME FAST SEPARATION OF MULTI-PHASE COMPONENTS IN FLUID SUSPENSIONS

(71) Applicant: FloDesign Sonics, Inc., Wilbraham, MA (US)

(72) Inventors: Jason Dionne, Simsbury, CT (US); Bart Lipkens, Hampden, MA (US); Edward Rietman, Nashua, NH (US)

(73) Assignee: FloDesign Sonics, Inc., Wilbraham, MA (US)

( * ) Notice: Subject to any disclaimer, the term of this patent is extended or adjusted under 35 U.S.C. 154(b) by 12 days.

This patent is subject to a terminal disclaimer.

(21) Appl. No.: 15/245,044

(22) Filed: Aug. 23, 2016

(65) Prior Publication Data

US 2016/0368000 A1 Dec. 22, 2016

Related U.S. Application Data

(63) Continuation of application No. 13/216,049, filed on Aug. 23, 2011, now Pat. No. 9,421,553.

(Continued)

(51) Int. Cl.
*B03B 5/00* (2006.01)
*C02F 1/36* (2006.01)
(Continued)

(52) U.S. Cl.
CPC .............. *B03B 5/00* (2013.01); *B01D 21/283* (2013.01); *C02F 1/36* (2013.01); *C12M 47/02* (2013.01); *B01D 21/28* (2013.01)

(58) Field of Classification Search
CPC ........ B01D 21/28; B01D 21/283; B03B 5/00; C02F 1/34; C02F 1/36

(Continued)

(56) References Cited

U.S. PATENT DOCUMENTS 2,473,971 A 6/1949 Ross
2,667,944 A 2/1954 Crites
(Continued)

FOREIGN PATENT DOCUMENTS

DE 30 27 433 A1 2/1982
DE 196 48 519 A1 6/1998
(Continued)

OTHER PUBLICATIONS

Alvarez et al.; Shock Waves, vol. 17, No. 6, pp. 441-447, 2008.
(Continued)

*Primary Examiner* — Joseph C Rodriguez
*Assistant Examiner* — Kalyanavenkateshware Kumar
(74) *Attorney, Agent, or Firm* — Rick Klein, Esq.; Fay Sharpe, LLP

(57) ABSTRACT

A flow chamber is provided through which is flowed a mixture of a fluid and a particulate. The flow chamber comprises at least one multi-phase water inlet through which multi-phase water enters the flow chamber, a water outlet through which water exits the flow chamber, a solids outlet through which particles having a density at or above a pre-defined threshold exit the flow chamber, and a low density outlet through which particles having a density below the pre-defined threshold exit the flow chamber. Also provided are one or more ultrasonic transducers and one or more reflectors corresponding to each transducer to acoustically filter the fluid and cause particles/fluid to be selectively diverted to one of the outlets. Related apparatus, systems, techniques and articles are also described.

20 Claims, 11 Drawing Sheets

Related U.S. Application Data

(60) Provisional application No. 61/402,079, filed on Aug. 23, 2010.

(51) Int. Cl.
    *B01D 21/28* (2006.01)
    *C12M 1/00* (2006.01)

(58) Field of Classification Search
    USPC .......... 209/155, 156; 422/20, 292, 306; 210/748.01–748.05, 321.6–321.9
    See application file for complete search history.

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Sma |
| 4,118,649 A | 10/1978 | Schwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,320,659 A | 3/1982 | Lynnworth et al. |
| 4,344,448 A | 8/1982 | Potts |
| 4,398,325 A | 8/1983 | Piaget et al. |
| 4,666,595 A | 5/1987 | Graham |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,878,210 A | 10/1989 | Mitome |
| 4,983,189 A | 1/1991 | Peterson et al. |
| 5,164,094 A | 11/1992 | Stuckart |
| 5,225,089 A | 7/1993 | Benes et al. |
| 5,371,729 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,649,069 B2 | 11/2003 | DeAngelis |
| 6,699,711 B1 | 3/2004 | Hahn et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2007/0272618 A1 | 11/2007 | Gou et al. |
| 2007/0284299 A1 | 12/2007 | Xu et al. |
| 2008/0105625 A1 | 5/2008 | Rosenberg et al. |
| 2008/0217259 A1 | 9/2008 | Siversson |
| 2008/0245709 A1 | 10/2008 | Kaduchak et al. |
| 2008/0272034 A1 | 11/2008 | Ferren et al. |
| 2008/0272065 A1 | 11/2008 | Johnson |
| 2009/0029870 A1 | 1/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0178716 A1 | 7/2009 | Kaduchak et al. |
| 2009/0194420 A1 | 8/2009 | Mariella, Jr. et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |

(56) References Cited

U.S. PATENT DOCUMENTS

| | | | |
|---|---|---|---|
| 2011/0125024 | A1 | 5/2011 | Mueller |
| 2011/0146678 | A1 | 6/2011 | Ruecroft et al. |
| 2011/0154890 | A1 | 6/2011 | Holm et al. |
| 2011/0166551 | A1 | 7/2011 | Schafer |
| 2011/0189732 | A1 | 8/2011 | Wienand et al. |
| 2011/0262990 | A1 | 10/2011 | Wang et al. |
| 2011/0278218 | A1 | 11/2011 | Dionne et al. |
| 2011/0281319 | A1 | 11/2011 | Swayze et al. |
| 2011/0309020 | A1 | 12/2011 | Rietman et al. |
| 2012/0088295 | A1 | 4/2012 | Yasuda et al. |
| 2012/0163126 | A1 | 6/2012 | Campbell et al. |
| 2012/0175012 | A1 | 7/2012 | Goodwin et al. |
| 2012/0267288 | A1 | 10/2012 | Chen et al. |
| 2012/0325727 | A1 | 12/2012 | Dionne et al. |
| 2012/0325747 | A1 | 12/2012 | Rietman et al. |
| 2012/0328477 | A1 | 12/2012 | Dionne et al. |
| 2012/0329122 | A1 | 12/2012 | Lipkens et al. |
| 2013/0115664 | A1 | 5/2013 | Khanna et al. |
| 2013/0175226 | A1 | 7/2013 | Coussios et al. |
| 2013/0217113 | A1 | 8/2013 | Srinivasan et al. |
| 2013/0277316 | A1 | 10/2013 | Dutra et al. |
| 2013/0277317 | A1 | 10/2013 | LoRicco et al. |
| 2013/0284271 | A1 | 10/2013 | Lipkens et al. |
| 2014/0011240 | A1 | 1/2014 | Lipkens et al. |
| 2014/0017758 | A1 | 1/2014 | Kniep et al. |
| 2014/0319077 | A1 | 10/2014 | Lipkens et al. |

FOREIGN PATENT DOCUMENTS

| | | |
|---|---|---|
| DE | 10 2008 006 501 A1 | 9/2008 |
| EP | 0 292 470 B1 | 11/1988 |
| EP | 1 254 669 B1 | 11/2002 |
| GB | 2 420 510 A | 5/2006 |
| JP | 9-136090 | 5/1997 |
| WO | WO 1987/07178 A1 | 12/1987 |
| WO | WO 90/05008 | 3/1990 |
| WO | WO 98/50133 A1 | 11/1998 |
| WO | WO 02/072234 A1 | 9/2002 |
| WO | WO 2004/079716 A1 | 9/2004 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043297 A1 | 3/2013 |
| WO | WO 2013/055517 A1 | 4/2013 |
| WO | WO 2014/014941 A1 | 1/2014 |
| WO | WO 2014/055219 A2 | 4/2014 |
| WO | WO 2014/124306 A1 | 8/2014 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanbiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNANO.2009.177.

Seymour et al, J. Chem. Edu., 1990, 67(9), p. 763, published Sep. 1990.

Wang et al.; Retention and Viability Characteristics of Mammalian Cells in an Acoustically Driven Polymer Mesh; Biotechnol. Prog. 2004, pp. 384-387 (2004).

Annex to Form PCT/ISA/206—Communication Relating to the Results of the Partial International Search Report, dated Jul. 18, 2013.

European Search Report of European Application No. 11769474.5, dated Sep. 5, 2013.

European Search Report of European Application No. 13760840.2, dated Feb. 4, 2016.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

International Search Report and Written Opinion of International Application No. PCT/US2012/051804 dated Nov. 16, 2012.

International Search Report and Written Opinion of International Application No. PCT/US2013/037404 dated Jun. 21, 2013.

International Search Report and Written Opinion of International Application No. PCT/US2013/032705 dated Jul. 26, 2013.

International Search Report and Written Opinion of International Application No. PCT/US2013/050729 dated Sep. 25, 2013.

International Search Report dated Feb. 18, 2014 in corresponding PCT Application No. PCT/US2013/059640.

International Search Report for corresponding PCT Application Serial No. PCT/US2014/015382 dated May 6, 2014.

International Search Report for PCT/US2014/035557 dated Aug. 27, 2014.

International Search Report for PCT/US2014/043930 dated Oct. 22, 2014.

International Search Report for PCT/US2014/046412 dated Oct. 27, 2014.

(56) References Cited

OTHER PUBLICATIONS

International Search Report for PCT/US2014/064088 dated Jan. 30, 2015.
Extended European Search Report for Application No. EP 128338597 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report dated Jul. 30, 2015 for International Application No. PCT/US2015/030009.
International Search Report for PCT/US2015/039125 dated Sep. 30, 2015.
European Search Report of European Application No. 11796470.0 dated Jan. 5, 2016.
International Search Report and Written Opinion for International Application No. PCT/US2015/066884, dated Mar. 22, 2016.
International Search Report and Written Opinion for International Application No. PCT/US2016/024082 dated Jun. 27, 2016.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html.

FIG. 4A Iron-Oxide (20 μm)
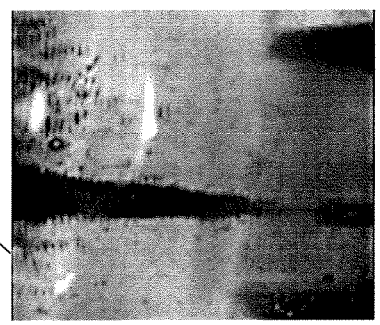
FIG. 4B Microalgae (10 μm)
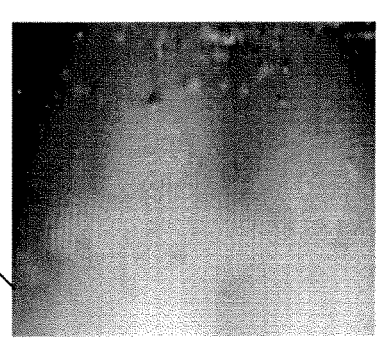
FIG. 4C Bacterial Spores (1 μm)
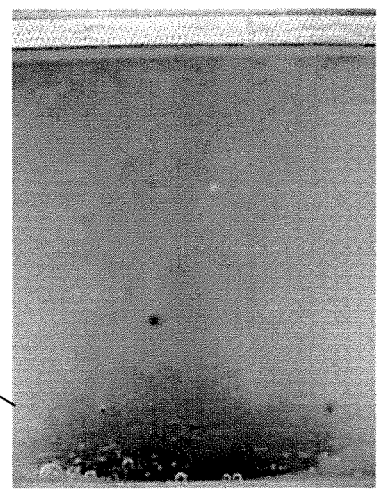
FIG. 4D Oil separation

HIGH-VOLUME FAST SEPARATION OF MULTI-PHASE COMPONENTS IN FLUID SUSPENSIONS

CROSS-REFERENCE TO RELATED APPLICATIONS

This application is a continuation of U.S. patent application Ser. No. 13/216,049, filed Aug. 23, 2011, which claims priority to U.S. patent application Ser. No. 61/402,079, filed on Aug. 23, 2010, the contents of which are hereby fully incorporated herein by reference.

TECHNICAL FIELD

The subject matter described herein relates to techniques for separating multiphase components within fluid suspensions such as water.

BACKGROUND

Numerous processes require the removal of solids, microorganisms, and oils that are suspended in a water matrix. For example, water can include suspended oils and dirt which must be removed for human use either for irrigation, or industrial processes, or recycling. However, accurate removal or separation of particles from water can be costly and/or time consuming especially when high volumes of water are being treated.

SUMMARY

In one aspect, a flow chamber is provided through which is flowed a mixture of a fluid and a particulate. The flow chamber comprises at least one multi-phase water inlet through which multi-phase water enters the flow chamber, a water outlet through which water exits the flow chamber, a solids outlet through which particles having a density at or above a pre-defined threshold exit the flow chamber, and a low density outlet through which particles having a density below the pre-defined threshold exit the flow chamber. Also provided are one or more ultrasonic transducers and one or more reflectors corresponding to each transducer. Each transducer forms a standing acoustic wave at a different ultrasonic frequency and each ultrasonic frequency is optimized for a specific range of particle sizes to, along with a geometry of the flow chamber, selectively separate particles from the multi-phase water and water so that such particles exit the flow chamber via one of the solids outlet and the low density outlet.

The one or more ultrasonic transducers operate at a frequency in a range of 1 MHz to 10 MHz, and in some implementations, the one or more ultrasonic transducers operate at a frequency in a range of 100 kHz to 20 MHz. The one or more ultrasonic transducers can be embedded in a wall of the flow chamber. The one or more ultrasonic transducers can be arranged in a flat series. In arrangements with multiple transducers, the transducers can be arranged in a parallel array within an inner portion of the flow chamber.

The flow chamber can be vertically oriented (relatively to gravity) with the low density outlet being on an upper portion and the solids outlet being on a lower portion. In other implementations, the flow chamber can be horizontally oriented with the low density outlet being on the upper portion and the solids outlet being on the lower portion. The flow chamber can alternatively be diagonally oriented with the low density outlet being on the upper incline and the solids outlet being on the lower incline. With a diagonal arrangement, the multi-phase water inlet can be at an obtuse angle from an outer wall of the flow chamber relative to the solids outlet.

The multi-phase water inlet can be disposed between the low density outlet and the two or more ultrasonic transducers. The multi-phase water inlet can be at an acute angle from an outer wall of the flow chamber relative to the solids outlet. The water outlet can be disposed between the two or more ultrasonic transducers and the solids outlet.

The particles can be selected from a group comprising: microalgae, yeast, fungi, bacteria, spores, gases or oils, metal oxides, metal particles, clays, dirt, plastics, and any particulate with a non-zero contrast factor. In arrangement with multiple transducers, each transducer can be optimized for a specific range of particles (which can be mutually exclusive) selected from a group consisting of microalgae, yeast, fungi, bacteria, spores, gases or oils, metal oxides, metal particles, clays, dirt, plastics, and any particulate with a non-zero contrast factor.

The one or more ultrasonic transducers can each generate acoustic standing waves perpendicular, to the direction of the mean flow in the flow channel. In other arrangements, the one or more acoustic standing waves have a or a vertical horizontal orientation. The one or more acoustic standing waves can exert acoustic radiation force on the particulate for which the ultrasonic frequency is optimized for, such that the particulate is trapped in its corresponding acoustic standing wave against a fluid drag force such that the particulate is concentrated in the acoustic field over time.

In addition, the solids outlet can be tapered. The flow chamber can be oriented such that the multi-phase water is gravity fed from the multi-phase water inlet towards the solids outlet.

In another aspect, a method of separating particulate from a fluid is provided that comprises: flowing the fluid past one or more positions within a flow chamber and forming acoustic standing waves at the one or more positions. In such an arrangement, each standing acoustic wave is maintained at a different ultrasonic frequency such that each ultrasonic frequency is optimized for a specific range of particle sizes and wherein particulate of the optimized size is trapped in its corresponding acoustic standing wave against the flow of the fluid, thereby concentrating the particulate in its corresponding acoustic standing wave. With such an arrangement, the flow chamber can comprise at least one multi-phase water inlet through which multi-phase water enters the flow chamber, a water outlet through which water exits the flow chamber, a solids outlet through which particles having a density at or above a pre-defined threshold exit the flow chamber, and a low density outlet through which particles having a density below the pre-defined threshold exit the flow chamber.

In yet another aspect, an apparatus includes a flow chamber through which is flowed a mixture of a fluid and a particulate. The flow chamber comprises at least one multi-phase water inlet through which multi-phase water enters the flow chamber, a water outlet through which water exits the flow chamber, a solids outlet through which agglomerated microorganisms and dirt exit the flow chamber, and a low density outlet through which agglomerated oil droplets exit the flow chamber. Also included can be one or more ultrasonic transducers, and one or more reflectors corresponding to each transducer. With this arrangement, each transducer forms a standing acoustic wave at a different ultrasonic frequency and each ultrasonic frequency is optimized for a specific range of particle sizes to, along with a geometry of the flow chamber, selectively separate particles from the multi-phase water and water so that such particles exit the flow chamber via one of the solids outlet and the low density outlet.

The current subject matter provides many advantages. For example, it allows for the efficient trapping, concentrating, and separation of various types of suspended particles, microorganisms and droplets from a host medium such as water.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 4A is a photograph of collected iron oxide using a system such as that illustrated in FIGS. 2-3;

FIG. 4B is a photograph of collected microalgae using a system such as that illustrated in FIGS. 2-3;

FIG. 4C is a photograph of collected bacterial spores using a system such as that illustrated in FIGS. 2-3;

FIG. 4D is a photograph of separated oil using a system such as that illustrated in FIGS. 2-3;

DETAILED DESCRIPTION

Figure 1:
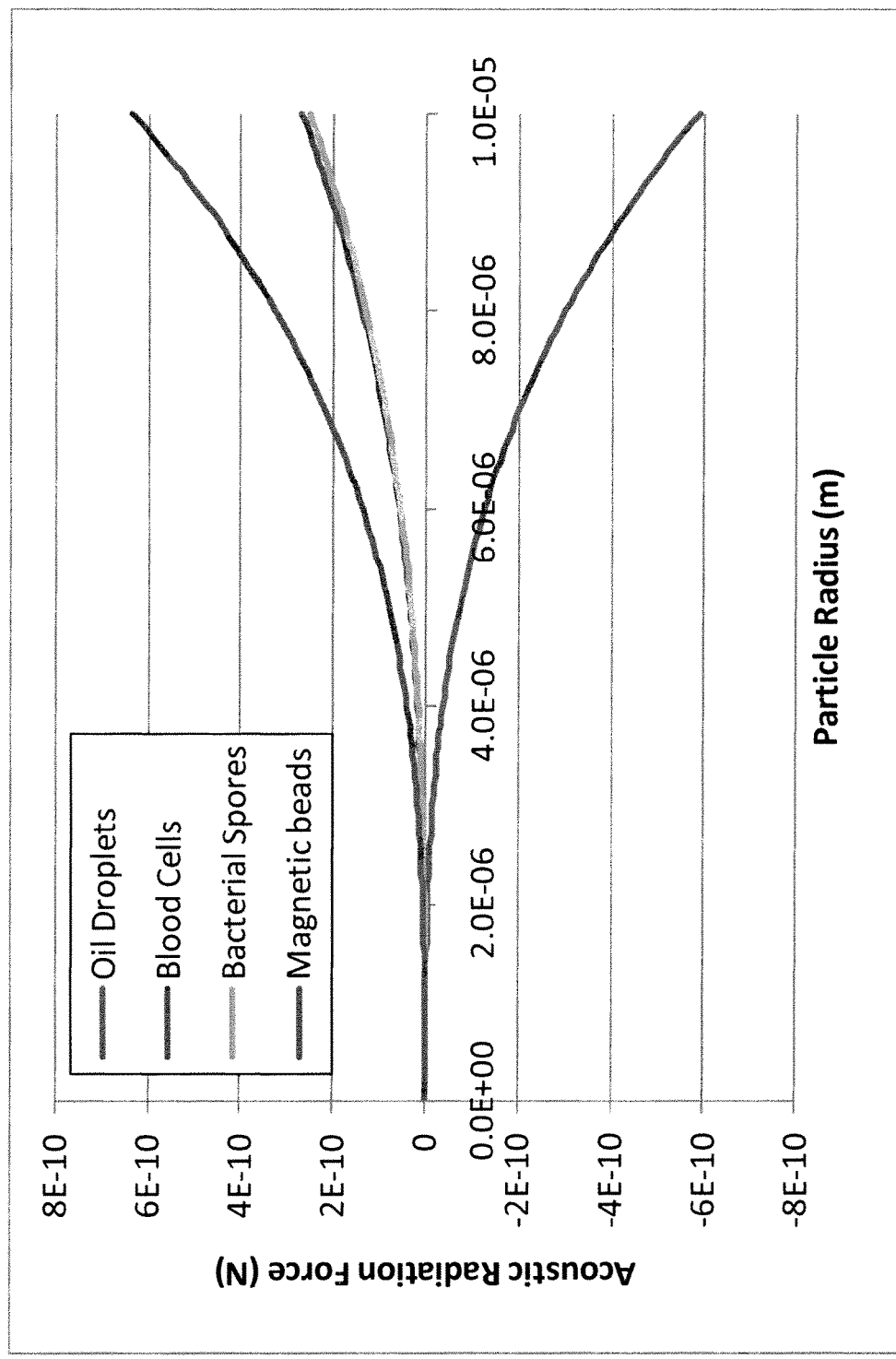
FIG. 1 is a diagram illustrating acoustic contrast, particle radius, and acoustic radiation force on particles for a given frequency of excitation and acoustic pressure level.
Figure 2:
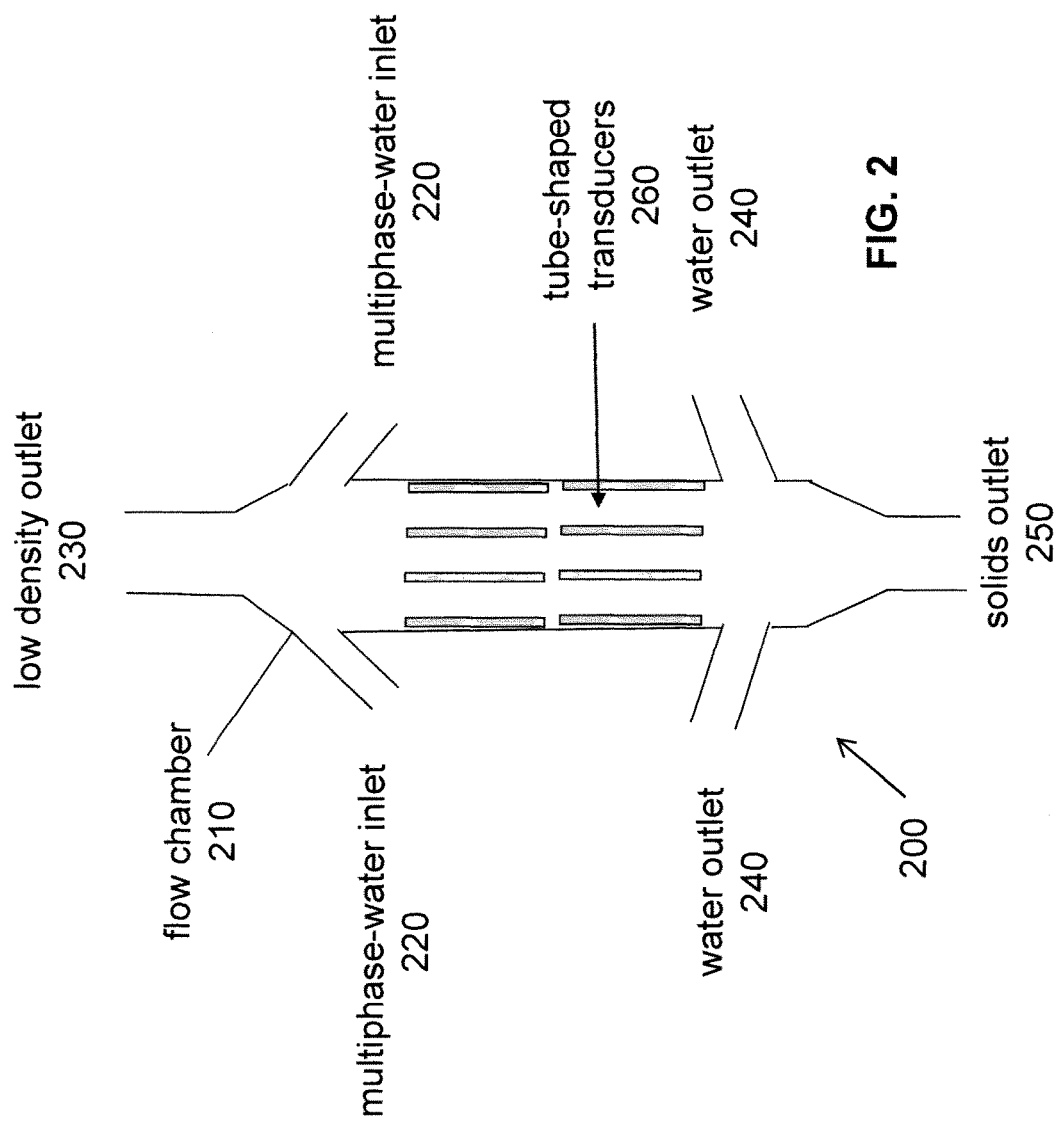
FIG. 2 is a schematic diagram of a first implementation having a parallel and/or serial array of tube-shaped transducers for agglomeration of and coalescence of suspended particles utilizing acoustic standing waves.
Figure 3:
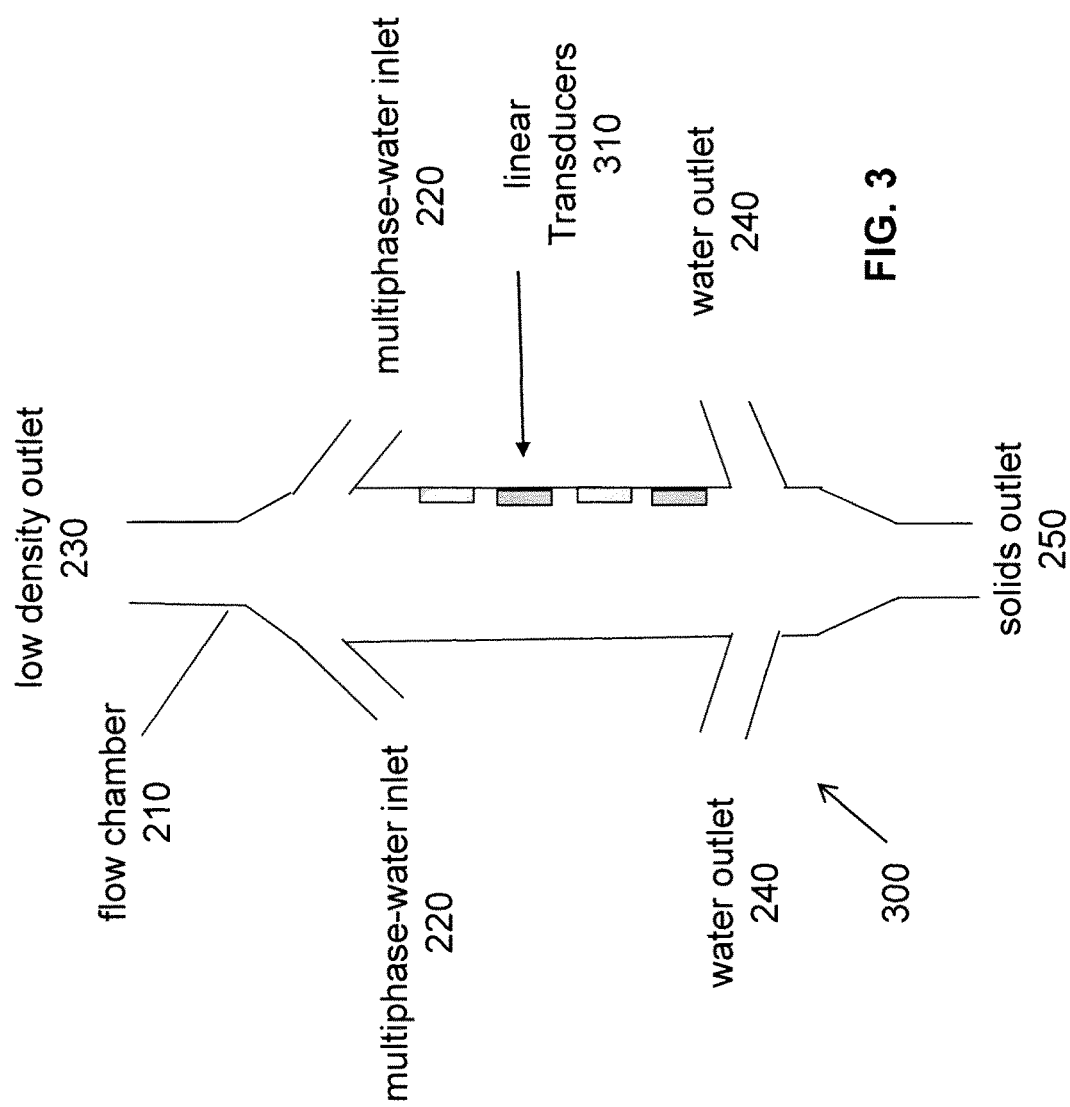
FIG. 3 is a schematic diagram of a second implementation in which there are flat transducers for agglomeration of and coalescence of suspended particles utilizing acoustic standing waves.

The current subject matter utilizes acoustophoresis, a low-power, no-pressure-drop, no-clog, solid-state approach to particle removal from fluid dispersions: i.e., it is used to achieve separations that are more typically performed with porous filters and centrifuges, but it has none of the disadvantages of these systems. For example, the diagram 100 of FIG. 1 shows the acoustic radiation forces acting on a suspended particle for an applied acoustic frequency of 1 MHz (typical for an ultrasonic transducer) and an acoustic pressure of 0.5 MPa maximum at the antinodes (readily achieved in water). Achievement of higher applied acoustic frequencies and higher acoustic pressures is possible with modern electronic drives, transducers, and intermediate matching layers. Examples of acoustic filters utilizing acoustophoresis can be found in commonly owned U.S. patent application Ser. Nos. 12/947,757, 61/261,686, 13/085,299 and 61/342,307, the contents of all of these applications are hereby fully incorporated by reference.

The acoustic radiation force ($F_{ac}$) acts on the secondary-phase particles (or fluid droplets), pushing them to the nodes (or antinodes) of the acoustic standing wave. The magnitude of the force depends on the particle density and compressibility relative to the fluid medium, and increases with the particle volume. The diagram 100 of FIG. 1 illustrates the acoustic force that operates on four different secondary phases in water as a function of the particle (or droplet) radius. The four secondary phases are hexanes (a mixture of hydrocarbons, a model for oils), red blood cells (a model for biological cells), bacterial spores (a model for "large" protein clusters and polystyrene beads such as are used for flow cytometry), and paramagnetic polystyrene beads (used for various biological capture and separation protocols). Parameters used in the calculation of the acoustic force are given below in Table 1.

The current subject matter is advantageous in that it uses acoustophoresis for separations in extremely high volumes and in flowing systems with very high flow rates. Separations have been done for micron-size particles, for which the acoustophoretic force is quite small. For example, B. Lipkens, J. Dionne, A. Trask, B. Szczur, A. Stevens, E. Rietman, "Separation of micron-sized particles in macro-scale cavities by ultrasonic standing waves," Presented at the International Congress on Ultrasonics, Santiago, Jan. 11-17, 2009; and B. Lipkens, J. Dionne, M. Costolo, A. Stevens, and E. Rietman, "Separation of bacterial spores from flowing water in macro-scale cavities by ultrasonic standing waves", (Arxiv) June 2010, the contents of both papers are hereby fully incorporated by reference) show that *Bacillus cereus* bacterial spores (a model for anthrax) have been trapped at 15% efficiency in an acoustophoretic cavity embedded in a flow system that can process drinking water at rates up to 120 mL/minute (1 cm/second linear flow). The concentration ratio has been as high as 1000 in a single-pass, small-scale prototype acoustocollector. The techniques described in this paper will scale up to higher flow rates or larger flow channel, which has been proven in a 6"×6" system and processing to 12" in dimension.

The current subject matter allows for the simultaneous agglomeration of suspended solids such as microorganisms and dirt (metal oxides) and oil droplets. The ability to translate and concentrate these secondary phases is known as acoustophoresis. Described herein is an improved flow chamber with two different ultrasonic transducer arrangements. Diagrams 200, 300 respectively of FIGS. 2-3, show two different transducer arrangements for two variations of an overall-view of the current systems which utilize a series of solid cylindrical and hollow cylindrical transducers with the flowing water for particle agglomeration. A small experimental system put together by the inventors that demonstrate the concept is described below.

With reference to FIGS. 2 and 3, a flow chamber 210 is illustrated having a multi-phase water inlet 220, a low density outlet 230, a water outlet 240, and a solids outlet 250. It will be appreciated that there may be two or more of each inlet and outlet depending on the desired configuration and volumes being processed. Multi-phase water (i.e., water having suspended particulate, etc.) enters from the multiphase water inlet 220 and exits as filtered water from water outlet 240. Particles and fluids having a low density, i.e., lower than the host fluid, such, as oils and other low-density fluids, exit from the low density outlet 230 and solids and other higher density particles exit from the solids outlet 250. An acoustic standing wave is generated in the middle of the flow chamber 210, either by a set of tube-shaped transducers 260 arranged in a parallel spacing within a center portion of the flow chamber or by an array of flat transducers 310, causes the particles (oil droplets) to agglomerate at the nodes (antinodes) in the acoustic wave. The agglomeration for high density particles will eventually result in their growing so as to overcome the acoustic pinning force and gravity settling causes them to fall into solids outlet 250. In the case of oil droplets the agglomeration at the antinodes will result in droplet coalescence and they will be able to overcome the acoustic pinning force and buoyancy force causes the larger droplets to drift to the low density outlet 230.

Several examples are shown in the photographs in FIGS. 4A-D. The first photo 410 shows the acoustophoretic collection of iron oxide particles, the second photograph 420 shows the collection of algae, the third photograph 430 shows the collection of bacterial spores, and the fourth photograph 440 shows the collection of oil droplets, all in a flowing water stream. A flat, circular transducer can, for example, be used in an acoustocollector to generate the collected matter in FIGS. 4A-D. The radial component of the pressure field of such a transducer is described by a Bessel function t whereas the axial component is described by a cosine function such as in the case of a one dimensional standing wave. The radial component acts to hold the captured algae in the column against the fluid flow drag force. The trapped algae are then further concentrated by inter-particles forces. The particles are then further separated from the flow by gravitational settling or by being driven to a collector pocket through a slow frequency sweeping method similar to that given in (i) B. Lipkens, M. Costolo, and E. Rietman, "The effect of frequency sweeping and fluid flow on particle trajectories in ultrasonic standing waves", IEEE Sensors Journal, Vol. 8, No. 6, pp. 667-677, 2008; (ii) Lipkens, J. Dionne, M. Costolo, and E. Rietman, "Frequency sweeping and fluid flow effects on particle trajectories in ultrasonic standing waves," Acoustics 08, Paris, Jun. 29-Jul. 4, 2008; and (iii) B. Lipkens, J. Dionne, A. Trask, B. Szczur, and E. Rietman, "Prediction and measurement of particle velocities in ultrasonic standing waves," J. Acoust. Soc. Am. 124, No. 4, pp. 2492 (A). The contents of each of the aforementioned papers are hereby fully incorporated by reference.

Physics of Acoustophoresis.

Acoustophoresis is the separation of a second phase (or phases) from a host fluid using sound pressure to create the driving force. An ultrasonic transducer operating at a fixed frequency f (Hz) is used to set up an acoustic standing wave in a fluid-filled cavity. A one dimensional standing wave is characterized by a local pressure p that is a function of position (x) and time (t), $$p(x,t) = P\cos(kx)\cos(\omega t), \quad (1)$$

where P is the amplitude of the acoustic pressure; k is the wavenumber ($=2\pi/\lambda$, where $\lambda$ is the wavelength), and $\omega = 2\pi f$, where $\omega$ is the angular frequency. The pressure of the acoustic wave produces an acoustic radiation force $F_{ac}$ on secondary-phase elements according to $$F_{ac} = X\pi R_p^3 k \frac{P^2}{\rho_f c_f^2} \sin(2kx), \quad (2)$$

where $R_p$ is the particle radius, $\rho_f$ is the density of the fluid medium, $c_f$ is the speed of sound in the fluid, and X is the acoustic contrast factor, defined by $$X = \frac{1}{3}\left[\frac{5\Lambda - 2}{1 + 2\Lambda} - \frac{1}{\sigma^2\Lambda}\right], \quad (3)$$

where $\Lambda$ is the ratio of the particle density to fluid density and $\sigma$ is the ratio of the speed of sound in the particle to the sound speed in the fluid. The acoustic radiation force acts in the direction of the acoustic field. The acoustic radiation force is proportional to the product of acoustic pressure and acoustic pressure gradient. An inspection of the acoustic radiation force shows that it is proportional to the particle volume, frequency (or wavenumber), the acoustic energy density (or the square of the acoustic pressure amplitude), and the acoustic contrast factor. Note also that the spatial dependency has twice the periodicity of the acoustic field. The acoustic radiation force is thus a function of two mechanical properties, namely density and compressibility.

TABLE 1

Properties of water and 4 selected secondary phases.

| Material | $\rho$ (density) (kg/m³) | c (speed of sound in the medium) (m/s) | $\Lambda$ (dimensionless) | X (dimensionless) |
|---|---|---|---|---|
| Water | 1000 | 1509 | — | — |
| Hexanes | 720 | 1303 | 0.72 | −0.402 |
| Blood Cells | 1125 | 1900 | 1.125 | 0.185 |
| Bacterial Spores | 1100 | 1900 | 1.1 | 0.173 |
| Magnetic beads | 2000 | 1971 | 2.0 | 0.436 |

For three dimensional acoustic fields, a more general approach for calculating the acoustic radiation force is needed. Gor'kov's (1962) formulation can be used for this (see L. P. Gor'kov, "On the forces acting on a small particle in an acoustical field in an ideal fluid," Sov. Phys. Dokl., vol. 6, pp. 773-775, 1962). Gor'kov developed an expression for the acoustic radiation force $F_{ac}$ applicable to any sound field. The primary acoustic radiation force is defined as the gradient of a field potential U, given by $$F_{ac} = -\nabla(U), \quad (4)$$

where the field potential U is defined as $$U = V_0\left[\frac{\langle p^2(x,y,t)\rangle}{2\rho_f c_f^2}f_1 - \frac{3\rho_f\langle v^2(x,y,t)\rangle}{4}f_2\right], \quad (5)$$

and $f_1$ and $f_2$ are the monopole and dipole contributions defined by $$f_1 = 1 - \frac{1}{\Lambda\sigma^2}, \quad (6)$$

$$f_2 = \frac{2(\Lambda - 1)}{2\Lambda + 1},$$

where p(x,y,z,t) is the acoustic pressure, v(x,y,z,t) is the fluid particle velocity, and < > denote time averages. $V_o$ is the volume of the particle.

The diagram 100 of FIG. 1 shows the force required to separate small particles of various material properties. Each material has its own X parameter given in Equation [3]. In diagram 100, material properties (e.g. speed of sound, density) are used for the indicated material. The graph for bacteria spore is also valid for other materials of similar bulk modulus. Meaning smaller bacteria spore, very large protein clusters, and polystyrene microspheres would all be in this category. The blood cell curve is for any cells of similar bulk modulus. Finally the hexane curve would be valid for any tiny drops of oil-like material with the radius indicated on the curve. These curves are for, as an example, 1 MHz applied acoustic frequency and an acoustic pressure of 0.5 MPa. These are easily achieved control variables. Higher frequency and higher pressure will afford better separation of smaller particles—down to 10 s of nm.

Simulations regarding the current subject matter were run by plotting the following equation:

$$\frac{n}{n_O} = \frac{\sin\left[2\text{arc }\tan\left[\exp\left[-4\left(\frac{2\pi f}{c}\right)^2 E_{ac}R^2Xt/(3\mu)\right]\tan\left(\frac{2\pi f}{c}\right)x\right]\right]}{\sin\left(\frac{4\pi f}{c}s\right)}$$

Where n is the number density of the suspended particulate, f is the frequency, c is the speed of sound, $E_{ac}$ is the energy density of the acoustic wave, R is the particle radius, X is the contrast factor, t is time, m is the dynamic viscosity of the fluid, and x is position in the standing wave. The equation describes the kinetics of the particles in the standing wave as a result of the action of the drag force and acoustic radiation force. This equation is derived in the paper by Feke et al.

The diagrams of FIGS. 5-10 plot the relative concentration, capture efficiency for different size particles of different densities and different frequencies. Along the x-axis is direction the particles travel from 0 to λ/2. The y-axis is the concentration relative to the initial of 1.

Figure 5:
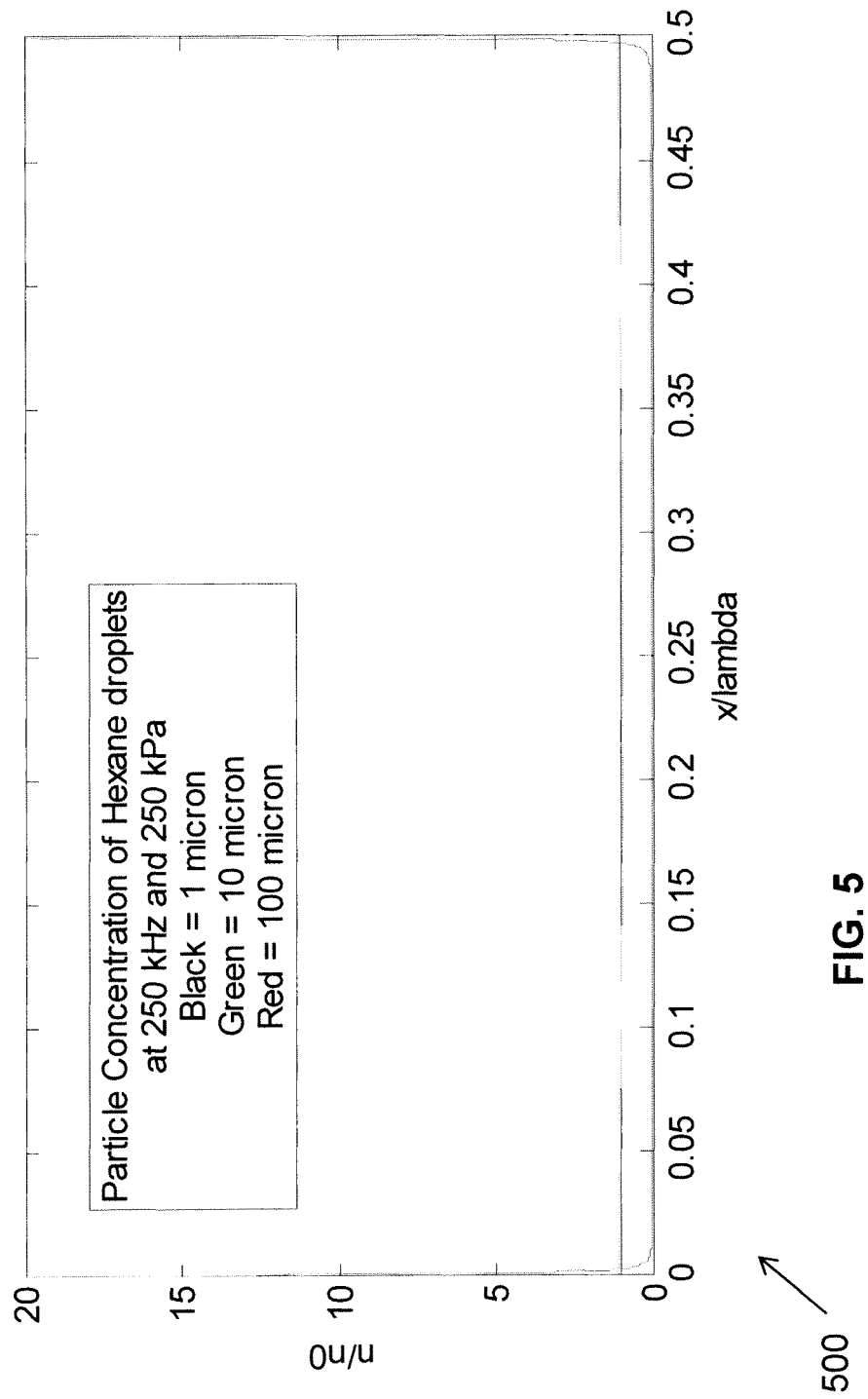
FIG. 5 is a diagram illustrating oil concentration at a transducer frequency of 250 kHz and exposure time of 0.1 s.
Figure 6:
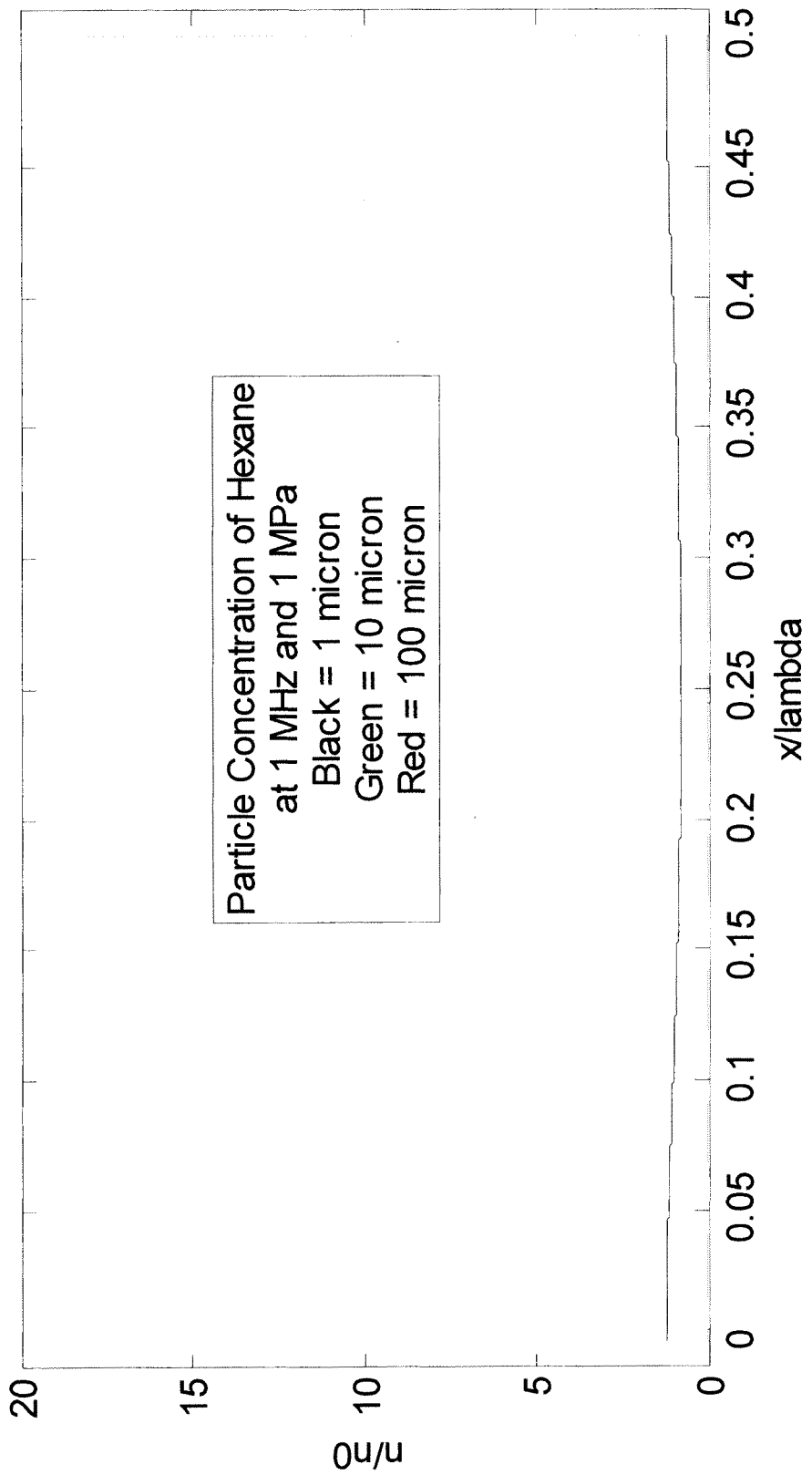
FIG. 6 is a diagram illustrating oil concentration at a transducer frequency of 1 MHz and exposure time of 0.1 s.
Figure 7:
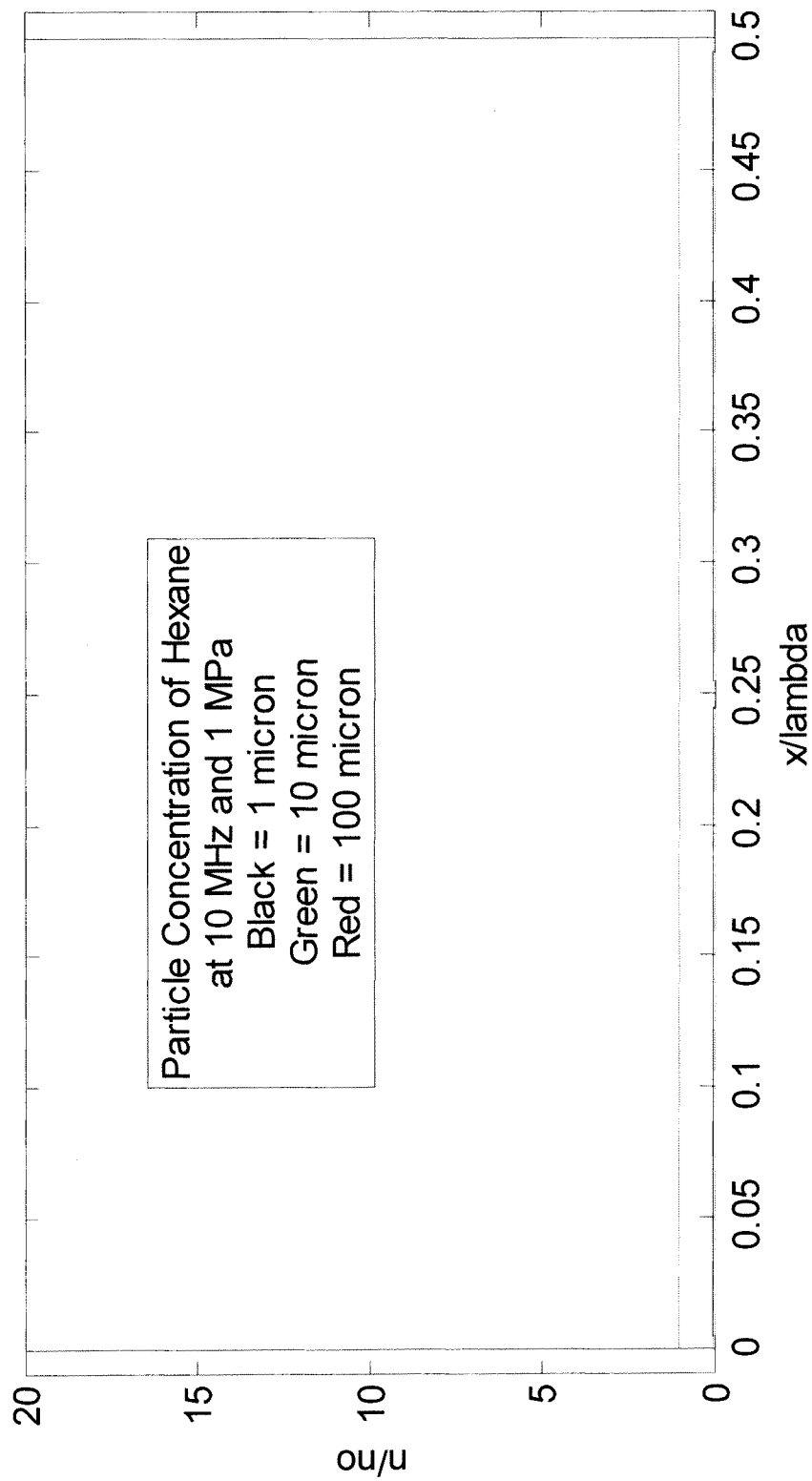
FIG. 7 is a diagram illustrating oil concentration at a transducer frequency of 10 MHz and exposure time of 0.1 s.

Diagram 500 of FIG. 5 shows the separation at 250 kHz for oil and an acoustic pressure amplitude of 250 kHz. Three particles sizes are shown; in black a 1 mm radius particle, in green a 10 mm radius particle, and in red a 100 mm radius particle. We see that the large droplets are heavily concentrated at the pressure anti-nodal planes of the standing wave, whereas the intermediate and small particle have not undergone any appreciable concentration. This situation can be used to selectively concentrate and separate large particles, and exhibits size-exclusion behavior. Diagram 600 of FIG. 6 shows separation at 1 MHz for oil. Here one can see a concentration efficiency of much greater than 20:1 for the intermediate and large droplets, and only minor changes for the small droplets. Finally, diagram 700 of FIG. 7 shows separation at 10 MHz, where the intermediate and small particles are heavily concentrated, but not the large ones. This is caused by the fact that the large particles are of the same order as the wavelength, and the acoustic radiation force is no longer effective. This is significant, because it shows a size-exclusion behavior that can be further exploited for preparation of very fine emulsions of biologically significant agents.

Figure 8:
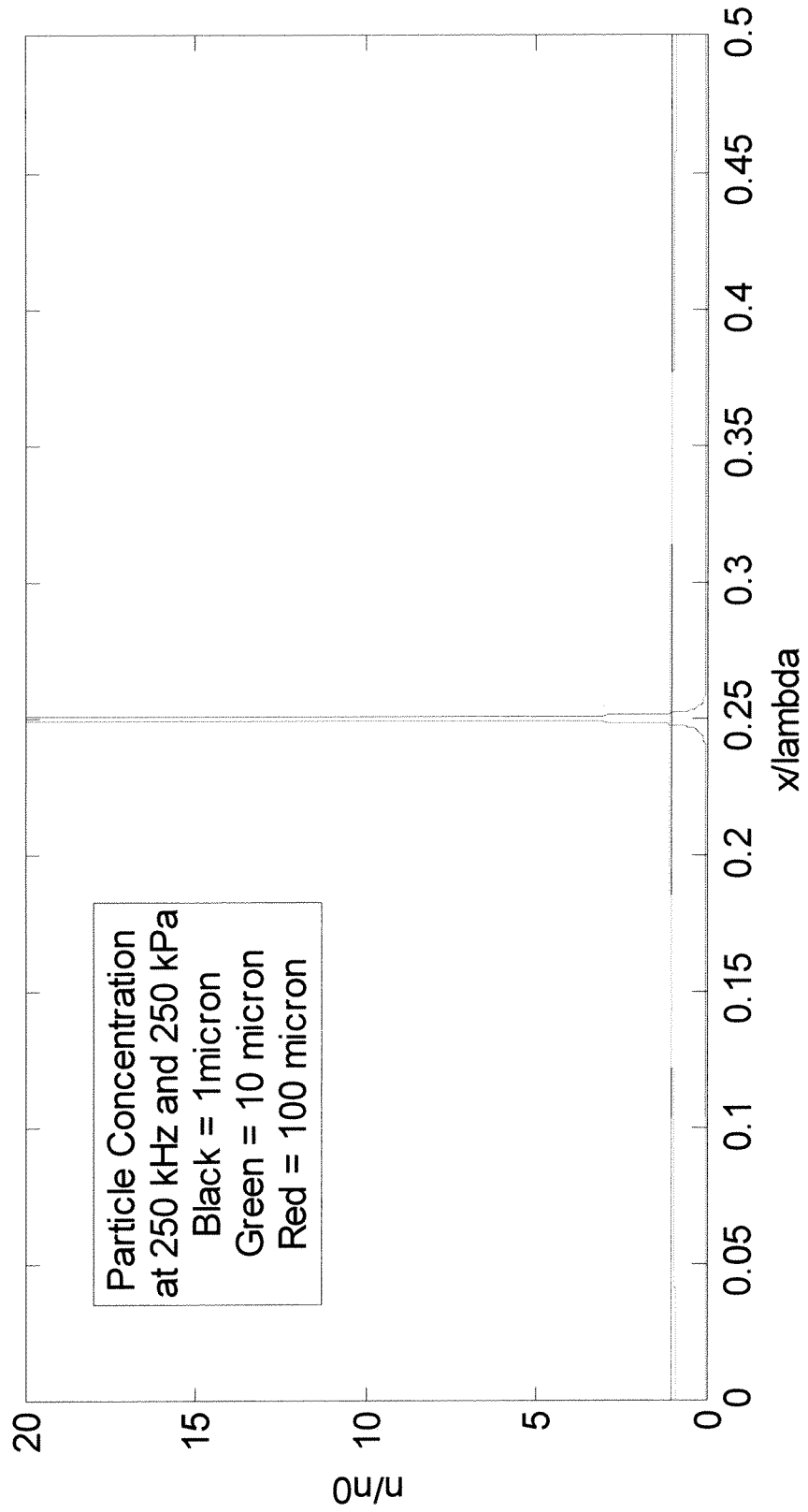
FIG. 8 is a diagram illustrating magnetic beads concentration at a transducer frequency of 250 kHz and exposure time of 0.1 s.
Figure 9:
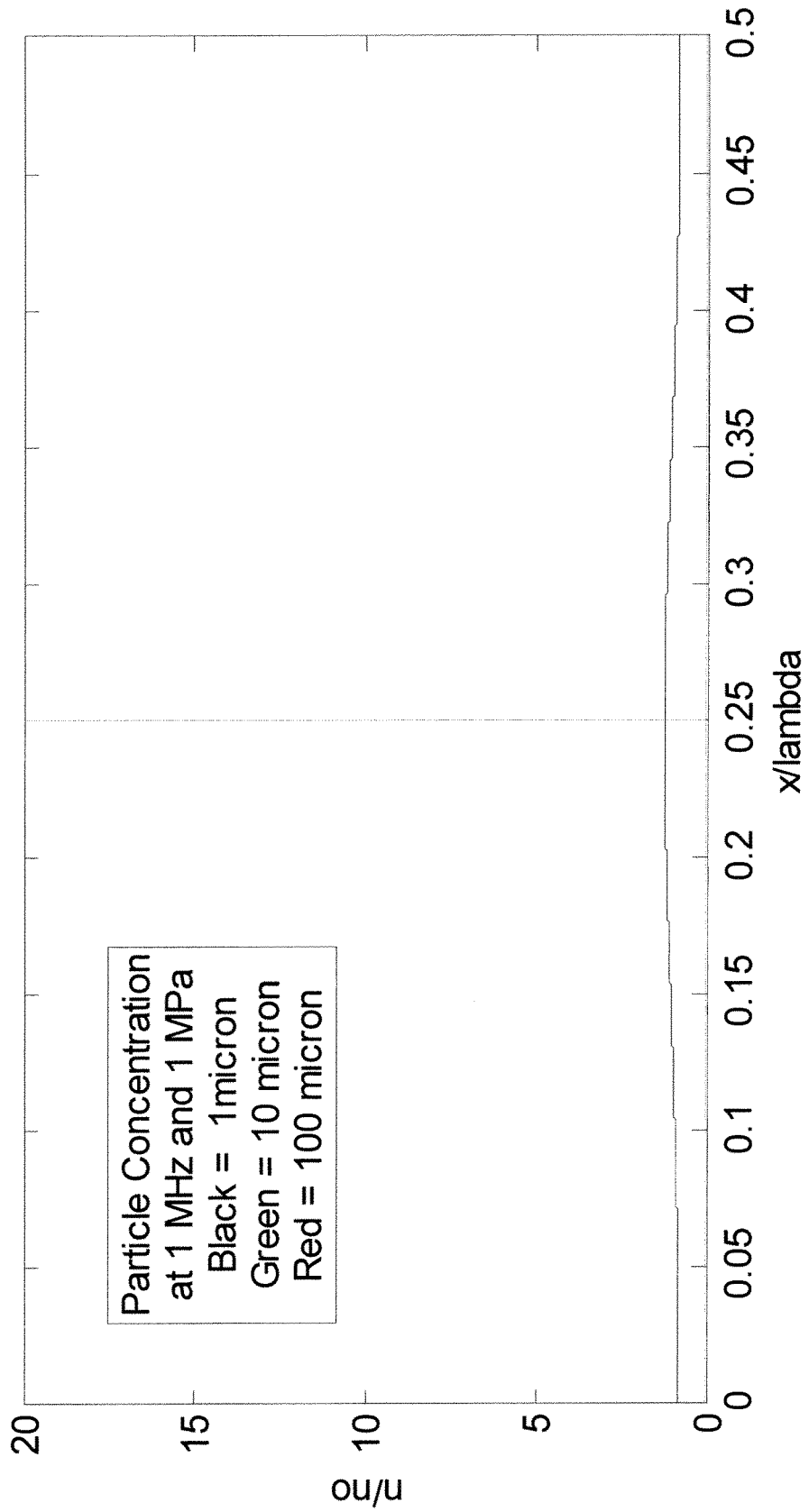
FIG. 9 is a diagram illustrating magnetic beads separation at a transducer frequency of 1 MHz and exposure time of 0.1 s.
Figure 10:
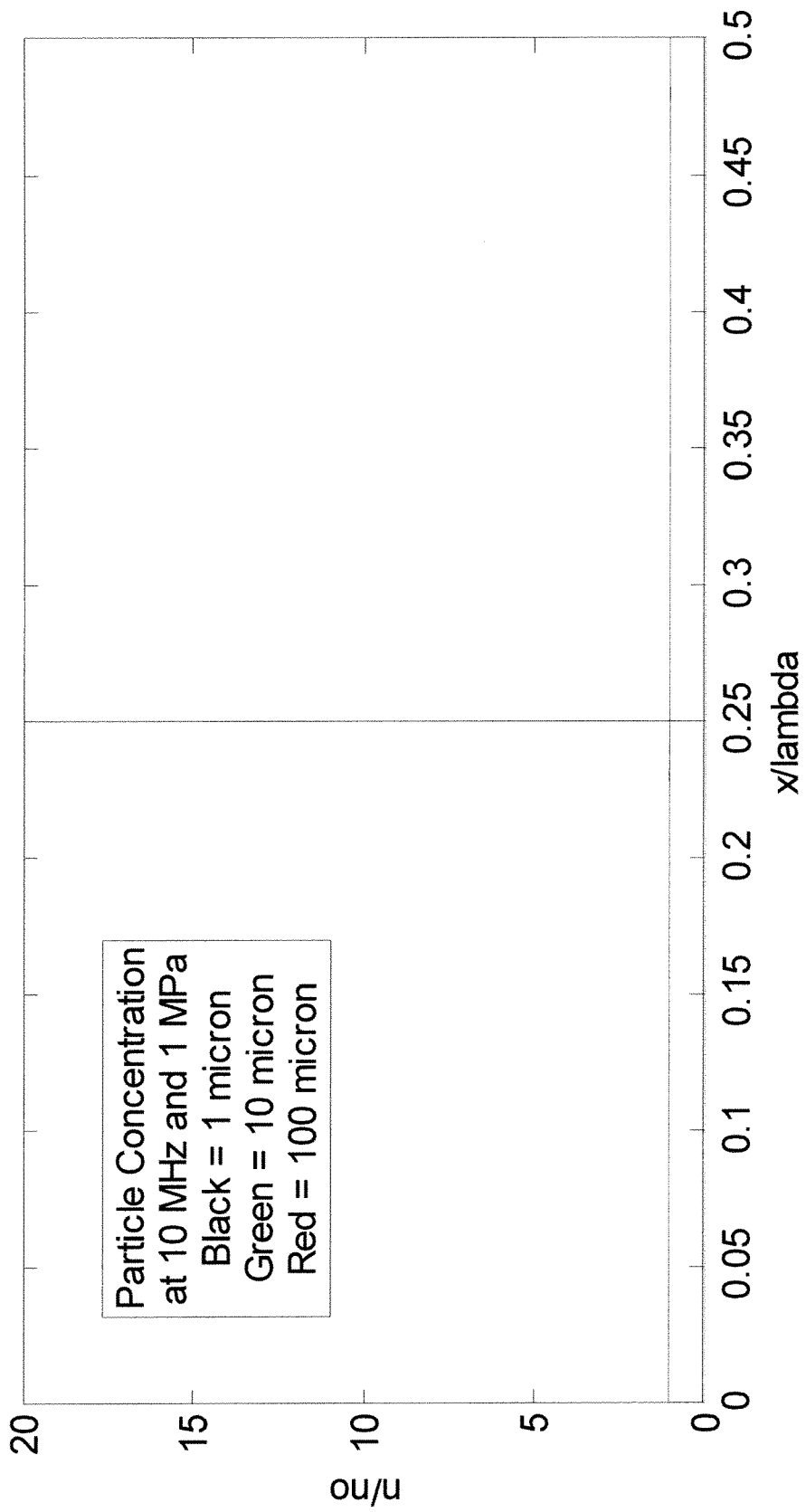
FIG. 10 is a diagram illustrating magnetic beads separation at a transducer frequency of 10 MHz and exposure time of 0.1 s.
Figure 11:
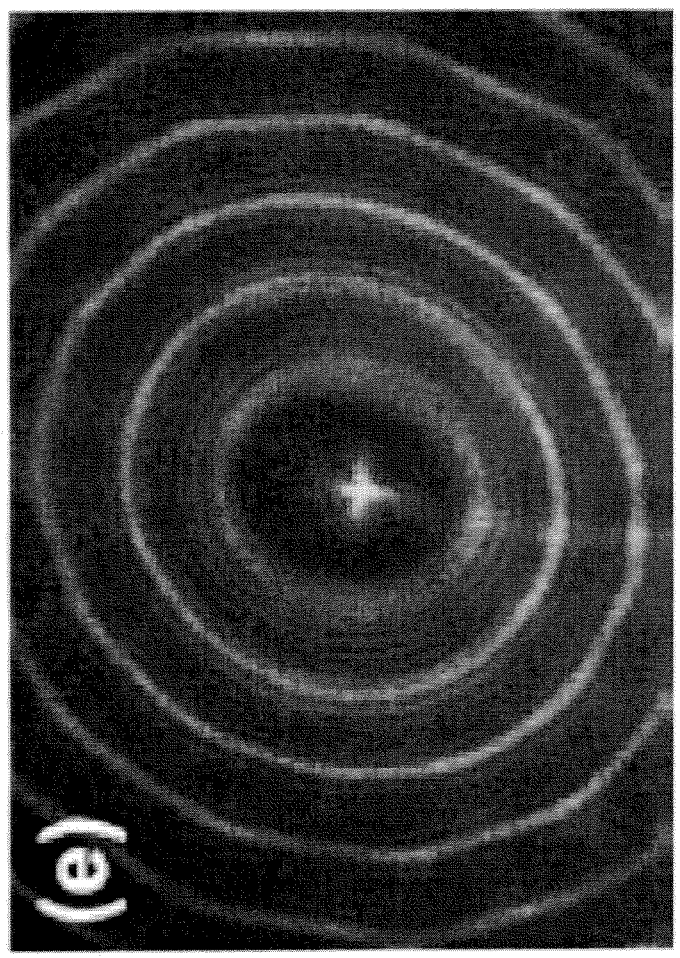
FIG. 11: is a photograph illustrating an acoustic standing wave in a tube shaped transducer.

FIGS. 8-10 show analogous conditions for iron oxide ($FeO_2$, a metal oxide simulant). Diagram 800 of FIG. 8 shows concentration at 250 kHz and 250 kPa for large, intermediate, and small particles of 100, 10, and 1 micron. We observe that particles with positive contrast move to the pressure nodes. It also shows that the large particles are concentrated significantly at the pressure nodes, and intermediate and smaller particles are not concentrated. Therefore, size-exclusion can work here as well. Diagram 900 of FIG. 9 shows the concentration at 1 MHz and 1 MPa, and shows that large and intermediate particles are concentrated but not small ones. Finally, diagram 1000 of FIG. 10 shows concentration at 10 MHz, where intermediate and small particles are concentrated. The large particles are of similar magnitude as the wavelength and do not experience significant concentration. Analogous behavior is observed for microalgae, bacteria, and blood cells. Like the oil case above, this is also significant because it demonstrates that the current subject matter can be applied for biotechnology applications for separating species of various sizes, essentially a high-flow, large-volume, size-exclusion separation technology. It also shows promise for lipid and platelet separation of blood.

As described above, two approaches to concentrating the particles through acoustic standing wave agglomeration (or coalescence). (1) The first approach as illustrated in FIG. 2 involves a series involves a parallel array of tube-shaped transducers. (2) The second approach as illustrated in FIG. 3 uses a series of flat acoustic transducers operating at 1 MHz and 10 MHz. Notwithstanding, it will be appreciated that other arrangements of acoustic transducers can be utilized.

The first implementation is shown in FIG. 2 with further details in the diagram 1100 of FIG. 11. With this arrangement, a multiphase-water mixture is pumped into the flow chamber 210 via the multi-phase water inlet 220 device from the where it encounters a parallel array of tube-shaped transducers 260 each operating at 1-10 MHz frequency. When the solution encounters the array of tube transducers 260 the agglomeration occurs and due to gravity the large clumps fall into the solids outlet 250 (e.g., a collection port, etc.). Any coalesced oil, or oil-like substances, will overcome buoyancy and self-transport to the respective low density outlet 230 on the top of the flow chamber 210. Diagram 1100 of FIG. 11 shows pressure nodes in the tube-shaped transducer array 260.

With the second approach, as shown in FIG. 3, a multiphase-water mixture is pumped into the flow chamber 210 via the multi-phase water inlet 220 where it encounters a serial array of flat 1 cm transducers 310 operating at a frequency range between 1 and 10 MHz. Like the first approach, when the solution encounters the array of tube transducers 310 the agglomeration occurs and due to gravity the large clumps fall into the solids outlet 250 (e.g., a collection port, etc.). Any coalesced oil, or oil-like substances, will overcome buoyancy and self-transport to the low density outlet 230 on the top of the flow chamber 210. As used herein, unless otherwise stated, the term outlet can comprise a piped exit from the flow chamber 210 or it can comprise a collection port requiring periodic removal of separated particulate.

While this specification contains many specifics, these should not be construed as limitations on the scope of what is claimed or of what may be claimed, but rather as descriptions of features specific to particular variations. Certain features that are described in this specification in the context of separate variations can also be implemented in combination in a single variation. Conversely, various features that are described in the context of a single variation can also be implemented in multiple variations separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. An apparatus comprising:
   a flow chamber comprising:
   at least one multi-phase fluid inlet through which multi-phase fluid enters the flow chamber at a high volume flow rate;
   at least one solids outlet;
   one or more ultrasonic transducers; and
   one or more reflectors corresponding to each transducer;
   each transducer being configured to form a three-dimensional acoustic field at a different ultrasonic frequency and each ultrasonic frequency being configured for a specific range of particulate sizes to, along with a geometry of the flow chamber, selectively separate particulates or droplets having a density at or above a pre-defined threshold from the multi-phase fluid by trapping the particulates or droplets in the three-dimensional acoustic field so that they agglomerate, coalesce, cluster, clump, or grow and increase in size such that they continuously fall out of the acoustic field and exit the flow chamber via the at least one solids outlet.

2. The apparatus of claim 1, wherein the one or more ultrasonic transducers operate at a frequency in a range of 100 kHz to 20 MHz.

3. The apparatus of claim 1, further comprising:
   a fluid outlet through which fluid exits the flow chamber;
   a low density outlet through which particulates or droplets having a density below the pre-defined threshold exit the flow chamber.

4. The apparatus of claim 3, wherein the multi-phase fluid inlet is disposed between the low density outlet and the one or more ultrasonic transducers.

5. The apparatus of claim 3, wherein the fluid outlet is disposed between the one or more ultrasonic transducers and the at least one solids outlet.

6. The apparatus of claim 3, wherein the flow chamber is oriented such that the multi-phase fluid is gravity fed from the multi-phase fluid inlet towards the solids outlet.

7. The apparatus of claim 1, wherein the particles are selected from the group consisting of microalgae, yeast, fungi, bacteria, spores, gases or oils, metal oxides, metal particles, clays, dirt, plastics, and any particulate with a nonzero contrast factor.

8. An apparatus comprising:
   a flow chamber comprising:
   at least one multi-phase fluid inlet through which multi-phase fluid enters the flow chamber at a high volume flow rate;
   at least one low density outlet;
   one or more ultrasonic transducers; and
   one or more reflectors corresponding to each transducer;
   each transducer being configured to form a three-dimensional acoustic field at a different ultrasonic frequency and each ultrasonic frequency being configured for a specific range of particulate sizes to, along with a geometry of the flow chamber, selectively separate particulates or droplets having a density below the pre-defined threshold from the multi-phase fluid by trapping the particulates or droplets in the three-dimensional acoustic field so that they agglomerate, coalesce, cluster, clump, or grow and increase in size such that they separate from the acoustic field and exit the flow chamber via the at least one low density outlet.

9. The apparatus of claim 8, wherein the one or more ultrasonic transducers operate at a frequency in a range of 100 kHz to 20 MHz.

10. The apparatus of claim 8, further comprising:
    a fluid outlet through which fluid exits the flow chamber; and
    a solids outlet through which particulates or droplets having a density at or above a pre-defined threshold exit the flow chamber.

11. The apparatus of claim 10, wherein the multi-phase fluid inlet is disposed between the at least one low density outlet and the one or more ultrasonic transducers.

12. The apparatus of claim 10, wherein the fluid outlet is disposed between the one or more ultrasonic transducers and the solids outlet.

13. The apparatus of claim 10, wherein the flow chamber is oriented such that the multi-phase fluid is gravity fed from the multi-phase fluid inlet towards the solids outlet.

14. The apparatus of claim 8, wherein the particles are selected from the group consisting of microalgae, yeast, fungi, bacteria, spores, gases or oils, metal oxides, metal particles, clays, dirt, plastics, and any particulate with a nonzero contrast factor.

15. An apparatus comprising:
    a flow chamber comprising:
    at least one multi-phase fluid inlet through which multi-phase fluid enters the flow chamber at a high volume flow rate;
    at least one fluid outlet;
    one or more ultrasonic transducers; and
    one or more reflectors corresponding to each transducer;
    each transducer being configured to form a three-dimensional acoustic field at a different ultrasonic frequency and each ultrasonic frequency being configured for a specific range of particulate sizes to, along with a geometry of the flow chamber, selectively separate particulates or droplets from the multi-phase fluid by trapping the particulates or droplets in the three-dimensional acoustic field, the remaining multi-phase fluid exiting the flow chamber via the at least one fluid outlet.

16. The apparatus of claim 15, further comprising:
    a solids outlet through which particulates or droplets having a density at or above a pre-defined threshold exit the flow chamber; and
    a low density outlet through which particulates or droplets having a density below the pre-defined threshold exit the flow chamber.

17. The apparatus of claim 16, wherein the flow chamber is oriented such that the multi-phase fluid is gravity fed from the multi-phase fluid inlet towards the solids outlet.

18. The apparatus of claim 15, wherein the particles are selected from the group consisting of microalgae, yeast, fungi, bacteria, spores, gases or oils, metal oxides, metal particles, clays, dirt, plastics, and any particulate with a nonzero contrast factor.

19. An apparatus comprising:

a flow chamber comprising:

at least one multi-phase fluid inlet through which multi-phase fluid enters the flow chamber at a high volume flow rate;

at least one outlet;

one or more ultrasonic transducers; and one or more reflectors corresponding to each transducer;

each transducer being configured to form a three-dimensional acoustic field at a different ultrasonic frequency and each ultrasonic frequency being configured for a specific range of particulate sizes to, along with a geometry of the flow chamber, selectively separate particulates or droplets from the multi-phase fluid by trapping the particulates or droplets in the three-dimensional acoustic field so that they agglomerate, coalesce, cluster, clump, or grow and increase in size such that they continuously separate from the acoustic field and exit the flow chamber via the at least one solids outlet.

20. A method of separating particulate and/or droplets from a multi-phase fluid, comprising:

flowing the multi-phase fluid through a flow chamber at a flow rate of up to 120 mL/min; and trapping particulates or droplets in a three-dimensional acoustic field against the flow of the multi-phase fluid within the flow chamber, each three-dimensional acoustic field being maintained at a different ultrasonic frequency, and each ultrasonic frequency being configured for a specific range of particulate or droplet sizes, such that the particulates or droplets agglomerate, coalesce, cluster, clump, or grow and increase in size such that they continuously fall out of the acoustic field due to gravity or rise out due to buoyancy forces and exit the flow chamber;

wherein the flow chamber comprises:

at least one multi-phase fluid inlet through which multi-phase fluid enters the flow chamber;

at least one outlet through which the particulate or droplet clusters exit the flow chamber;

one or more ultrasonic transducers configured to form the three-dimensional acoustic field; and one or more reflectors corresponding to each transducer.

* * * * *